(12) United States Patent
Lin

(10) Patent No.: US 10,982,340 B2
(45) Date of Patent: Apr. 20, 2021

(54) WATER ELECTROLYSIS DEVICE

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 94 days.

(21) Appl. No.: 16/108,823

(22) Filed: Aug. 22, 2018

(65) Prior Publication Data
US 2019/0062934 A1 Feb. 28, 2019

(30) Foreign Application Priority Data

Aug. 25, 2017 (CN) .......................... 201710739879.5

(51) Int. Cl.
| | | |
|---|---|---|
| *C25B 9/73* | (2021.01) | |
| *A61M 16/12* | (2006.01) | |
| *A61M 16/10* | (2006.01) | |
| *C25B 1/04* | (2021.01) | |
| *C25B 9/23* | (2021.01) | |
| *C25B 9/65* | (2021.01) | |
| *C25B 15/02* | (2021.01) | |
| *A61M 11/00* | (2006.01) | |

(52) U.S. Cl.
CPC .............. *C25B 9/73* (2021.01); *A61M 11/00* (2013.01); *A61M 16/10* (2013.01); *A61M 16/12* (2013.01); *C25B 1/04* (2013.01); *C25B 9/23* (2021.01); *C25B 9/65* (2021.01); *C25B 15/02* (2013.01); *Y02E 60/36* (2013.01)

(58) Field of Classification Search
CPC .................................................. C25B 1/02–10
See application file for complete search history.

(56) References Cited

U.S. PATENT DOCUMENTS

| | | | | |
|---|---|---|---|---|
| 2012/0222955 A1* | 9/2012 | Takeuchi | .................. | C25B 1/12 |
| | | | | 204/257 |
| 2015/0101601 A1 | 4/2015 | Lin | | |
| 2015/0190604 A1 | 7/2015 | Lin | | |

FOREIGN PATENT DOCUMENTS

| | | | |
|---|---|---|---|
| CN | 203291354 U | | 11/2013 |
| CN | 103670808 A | * | 3/2014 |
| CN | 106435633 | | 2/2017 |
| CN | 106906483 | | 6/2017 |
| JP | H08239788 | * | 3/1999 |
| JP | 2009005881 A | * | 1/2009 |
| JP | 20100189728 A | | 9/2010 |
| JP | 2016180177 A | | 10/2016 |

(Continued)

OTHER PUBLICATIONS

Search Report dated Nov. 12, 2018 for European Application No. 18189641.6.

*Primary Examiner* — Nicholas A Smith

(57) ABSTRACT

A water electrolysis device includes a membrane electrolyzer, an air supplying tube, and an air pump. The electrolyzer includes an ion-exchange membrane and a cathode chamber. A cathode electrode is configured in the cathode chamber. The cathode generates hydrogen gas while the electrolyzer electrolyzes water. The air pump draws air and is connected with the air supplying tube by a duct. A lead angle is formed between the duct and the air supplying tube for guiding the air from the duct into the air supplying tube to dilute the hydrogen concentration in the air supplying tube. The volume of the water electrolysis device is 8.5 liters, and the hydrogen gas generating rate of the water electrolysis device is located in a range between 120 ml/min and 600 ml/min.

18 Claims, 13 Drawing Sheets

(56) References Cited

FOREIGN PATENT DOCUMENTS

| | | | |
|---|---|---|---|
| JP | 2017012501 A | * | 1/2017 |
| TW | 201723233 | | 7/2017 |
| WO | WO2017020824 | | 2/2017 |

* cited by examiner

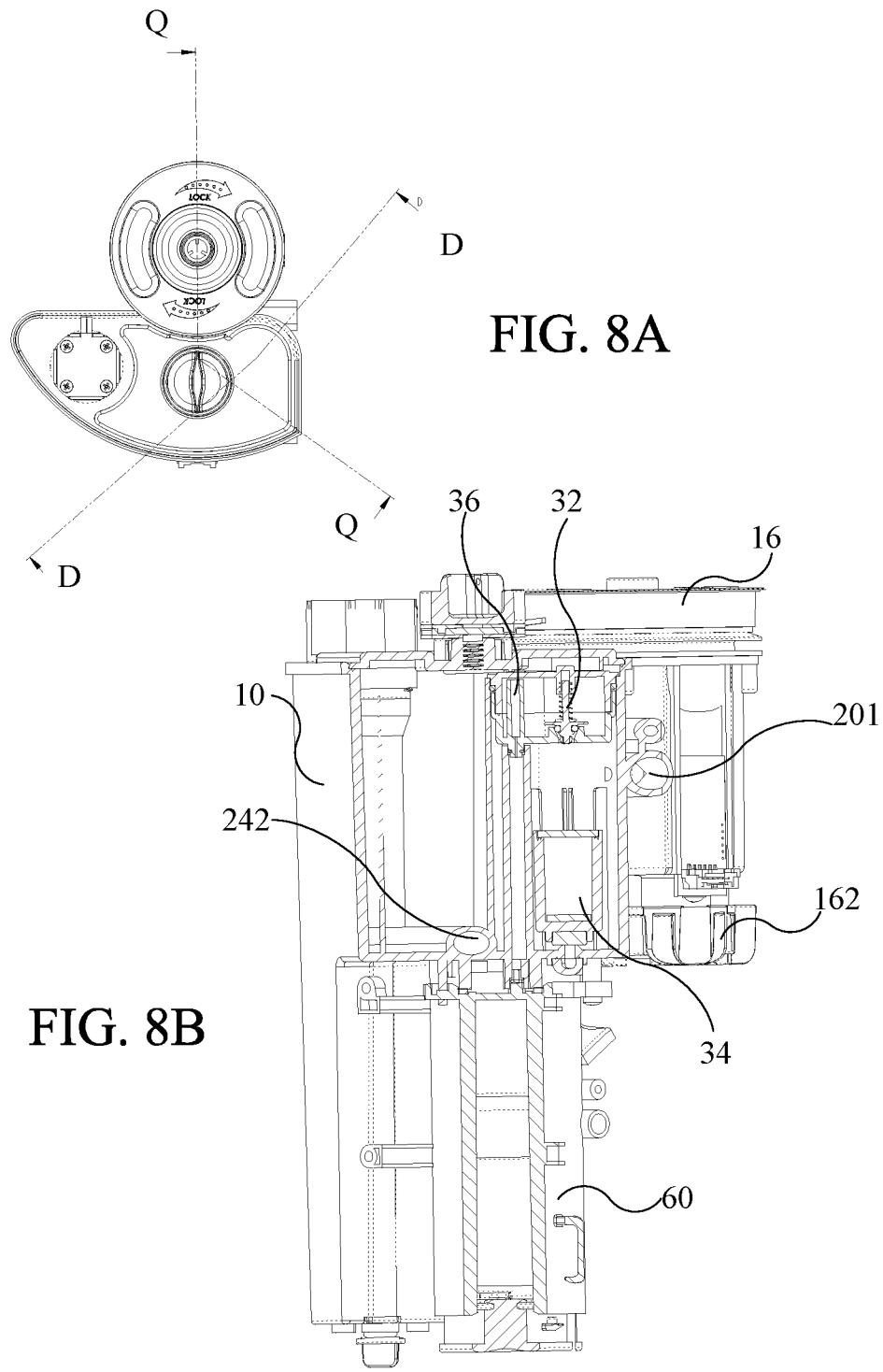

WATER ELECTROLYSIS DEVICE

CROSS-REFERENCE TO RELATED APPLICATIONS

This application claims the priority benefit of Chinese Application Serial No. 201710739879.5 filed Aug. 25, 2017 the disclosure of which is incorporated herein by reference.

BACKGROUND OF THE INVENTION

1. Field of the Invention

The present invention relates to a water electrolysis device, more specifically, to the water electrolysis device with an air pump which is connected to an air supplying tube by a duct and with a lead angle formed between the duct and the air supplying tube.

2. Description of the Prior Art

As people have been paying much attention on health developments, many developments in medical technology are often targeted on treating diseases to prolong human life. Most of the treatments in the past are passive; namely, diseases are treated only when they occur, which includes operations, medication treatments, radiation therapies, or even medical treatments for cancer. However, in recent years, most of the researches from medical experts are gradually being moved towards preventive medical methods, such as healthy food, screening and the prevention of inherited diseases, to actively prevent diseases from occurring in the future. Moreover, due to the focus of the prolongation of human life, many anti-aging and anti-oxidation technologies including skin care products and anti-oxidation food/medicine are gradually being developed and adopted by the general public.

Studies have found that there are instable oxygen species (O+), also known as free radicals, in the human body. The free radicals which are usually generated due to diseases, diet, environment and one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but this situation could be ameliorated by inhaling hydrogen In order to improve the effect of inhaling hydrogen gas, increasing the time of inhaling hydrogen gas is an effective way to improve the efficiency. In general, the conventional water electrolysis device is relatively bulky, and it is hard for a person to have enough time to inhale hydrogen gas beside the conventional water electrolysis device during daily activities. Therefore, inhaling hydrogen gas during sleep time could be an effective way. However, as mentioned above, the conventional water electrolysis device is relatively bulky, how to reduce the volume of the water electrolysis device and to maintain sufficient hydrogen gas production are the problems that must be solved.

In addition to the health care mentioned above, the use of hydrogen gas can also be used to generate an oxyhydrogen flame for heating or burning, and to remove engine carbon deposits and the like. In general, hydrogen gas is generated by the electrolyzing water in the electrolyzer. However, it is easy to cause high temperature during the process of electrolyzing water. In order to avoid gas explosion, the traditional hydrogen-oxygen electrolyzer is mostly air-cooled; namely, using a fan to cool down. However, if a trouble occurs on the fan, it will cause the temperature of the hydrogen-oxygen electrolyzer to rise and result in the danger of gas explosion. Furthermore, the hydrogen-oxygen mixed gas generated by electrolyzing water through the electrolysis device usually includes electrolyte, which is not suitable for human beings to inhale directly. At the same time, there is a problem of electrolyte consumption during the electrolysis process.

SUMMARY OF THE INVENTION

The present invention is to provide a water electrolysis device including an electrolyzer, an air supplying tube and an air pump. The electrolyzer includes a cathode. The cathode generates the hydrogen gas while the electrolyzer electrolyzes water. The air supplying tube is configured for receiving the hydrogen gas generated by the electrolyzer. The air pump draws air and is connected with the air supplying tube through an air supplying interface to dilute a hydrogen concentration in the air supplying tube. The air supplying tube includes the air supplying interface. The air pump includes a duct. A lead angle is formed on a connecting position between the air supplying interface and the air supplying tube to guide the air from the duct into the air supplying tube.

In one embodiment of the present invention, the air supplying tube has a first flow direction, and the air supplying interface has a second flow direction. The first flow direction points to the upper portion of the water electrolysis device. The second flow direction points to the air supplying tube. The lead angle is formed between the first flow direction and the second flow direction, wherein the range of the lead angle is preferably between 25 to 45 degrees. The shape of the connecting position with the lead angle is made as an arc lead angle.

In one embodiment of the present invention, the electrolyzer further includes an anode chamber and an oxygen output tube. The anode chamber includes an anode, an anode sealing plate, an anode conductive plate and an anode external plate. While the electrolyzer electrolyzes water, the anode chamber generates oxygen gas. The oxygen output tube is configured for outputting the oxygen gas. The oxygen output tube passes through the anode external plate, the anode conductive plate and the anode sealing plate.

In one embodiment of the present invention, the electrolyzer further includes a cathode chamber and a hydrogen output tube. The hydrogen output tube is configured for outputting the hydrogen gas. The cathode chamber includes a cathode, a cathode sealing plate and a cathode conductive plate. The hydrogen output tube passes through the anode external plate, the anode conductive plate, the anode sealing plate and the cathode sealing plate. The oxygen gas and the hydrogen gas are outputted from the same side of the ion-exchange membrane electrolyzer.

In one embodiment of the present invention, the electrolyzer further includes a water supplying pipe. The water supplying pipe is configured to pass through the anode external plate, the anode conductive plate and the anode sealing plate to connect to the anode chamber and a water tank. The water from the water tank flows into the anode chamber through the water supplying pipe to replenish electrolyzed water in the anode chamber.

In one embodiment of the present invention, the water electrolysis device further includes a water level detecting device. The water level detecting device is configured on the outer side of the water tank for detecting the amount of water in the water tank.

In one embodiment of the present invention, the water electrolysis device further includes a fan. The fan draws the air from the environment outside the water electrolysis device into the water electrolysis device, and the air pump draws the air and guides it into the air supplying tube.

In one embodiment of the present invention, the water electrolysis device further includes a hydrogen concentration detector which is connected to the air supplying tube for detecting whether the volume concentration of hydrogen gas in the air supplying tube is within a range from a first predetermined value to a second predetermined value. The hydrogen concentration detector generates a first warning signal when the detected volume concentration of hydrogen gas is higher than the first predetermined value. The water electrolysis device further includes a controller which is coupled to the hydrogen concentration detector, the air pump and the electrolyzer. The controller generates a start command to start up the air pump when receiving the first warning signal.

In one embodiment of the present invention, the hydrogen concentration detector generates a second warning signal when the detected volume concentration of hydrogen gas is higher than the second predetermined value. The controller generates a stop command to stop the electrolyzer when receiving the second warning signal.

In one embodiment of the present invention, the first predetermined value is 4%, the second predetermined value is 6%, and the range of the detected volume concentration of hydrogen gas in the air supplying tube is 4%~6%.

In one embodiment of the present invention, the water electrolysis device further includes an atomizing/volatile gas mixing tank which is connected to the air supplying tube to receive the diluted hydrogen gas. The atomizing/volatile gas mixing tank selectively generates an atomizing gas and mixes it with the hydrogen gas to form a health gas, wherein the atomizing gas is one or a combination selected from a group consisting of water vapor, atomizing potions and volatile essential oil.

In one embodiment of the present invention, the water electrolysis device further includes a power supply. The power supply includes a high power output and a low power output, wherein the electric power outputted by the low power output is equal to or less than half of that outputted by the high power output. The high power output outputs a first voltage and a first current. The low power output outputs a second voltage and a second current. The first voltage is less than the second voltage, and the first current is greater than the second current.

The present invention further provides another water electrolysis device including an electrolyzer, an air supplying tube and an air pump. The electrolyzer includes a cathode. The cathode generates hydrogen gas while the electrolyzer electrolyzes water. The air supplying tube is configured for receiving the hydrogen gas generated by the electrolyzer. The air pump draws air and is connected to the air supplying tube by an air supplying interface for receiving the air to dilute a hydrogen concentration in the air supplying tube. The volume of the water electrolysis device is less than 8.5 liter. The hydrogen generating rate of the water electrolysis device can be located in a range between 120 ml/min and 600 ml/min. The user is allowed to adjust the hydrogen generating rate of the water electrolysis device by an operation panel of the water electrolysis device.

In one embodiment of the present invention, the water electrolysis device further includes a case. The case includes a base and a side wall. The electrolyzer is configured in a non-central position of the case.

In one embodiment of the present invention, the electrolyzer includes a first side, a second side, an ion-exchange membrane, an anode, an oxygen output tube and a hydrogen output tube. The ion-exchange membrane is configured between the anode and the cathode. While the electrolyzer electrolyzes water, the cathode generates hydrogen gas, and the anode generates oxygen gas. The oxygen output tube is configured for outputting the oxygen gas. The hydrogen output tube is configured for outputting the hydrogen gas. The first side is close to the side wall, and both of the oxygen gas and the hydrogen gas are outputted from the second side of the electrolyzer.

In one embodiment of the present invention, the anode is configured between the ion-exchange membrane and the second side, and the cathode is configured between the ion-exchange membrane and the first side. The oxygen output tube extends from the position between the ion-exchange membrane and the second side to the second side and passes through the second side. The hydrogen output tube extends from the position between the ion-exchange membrane and the first side to the second side and passes through the second side.

In one embodiment of the present invention, the anode is configured between the ion-exchange membrane and the first side, and the cathode is configured between the ion-exchange membrane and the second side. The oxygen output tube extends from the position between the ion-exchange membrane and the first side to the second side and passes through the second side. The hydrogen output tube extends from the position between the ion-exchange membrane and the second side to the second side and passes through the second side.

By means of the electrolyzer with hydrogen gas and oxygen gas outputted from the same side, the water tank, the gas-water separation tank, the air supplying tube and the like, configured in the case with a limited volume, the present invention uses the containing space in the case as much as possible while maintaining sufficient hydrogen gas production and the low noise of the fan and the air pump. Therefore, the present invention actually provides a water electrolysis device with effective space arrangement, small volume, low noise and the suitableness for placement beside the user.

BRIEF DESCRIPTION OF THE APPENDED DRAWINGS

FIG. 8A is a top view drawing illustrating the water electrolysis device according to an embodiment of the present invention.

FIG. 8B is a sectional view drawing illustrating the water electrolysis device along the line D-D in FIG. 8A.

The advantages, spirits and features of the present invention will be explained and discussed in detail by way of the embodiments and with reference of the drawings.

DETAILED DESCRIPTION OF THE INVENTION

For the sake of the advantages, spirits and features of the present invention can be understood more easily and clearly, the detailed descriptions and discussions will be made later by way of the embodiments and with reference of the diagrams. It is worth noting that these embodiments are merely representative embodiments of the present invention, wherein the specific methods, devices, conditions, materials and the like are not limited to the embodiments of the present invention or corresponding embodiments.

Figure 1A:
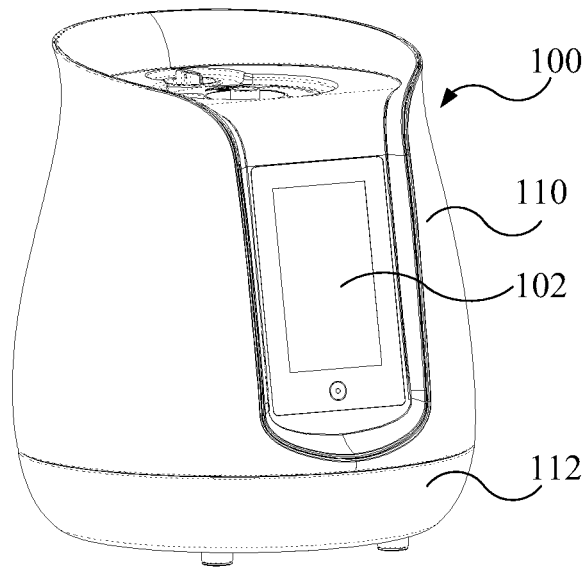
FIG. 1A is an appearance drawing illustrating a water electrolysis device according to an embodiment of the present invention.
Figure 1B:
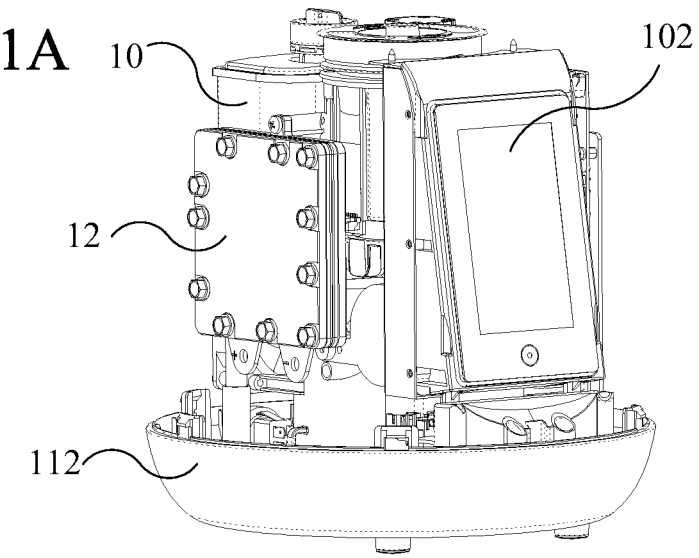
FIG. 1B is an appearance drawing illustrating the water electrolysis device without the case according to an embodiment of the present invention.
Figure 1C:
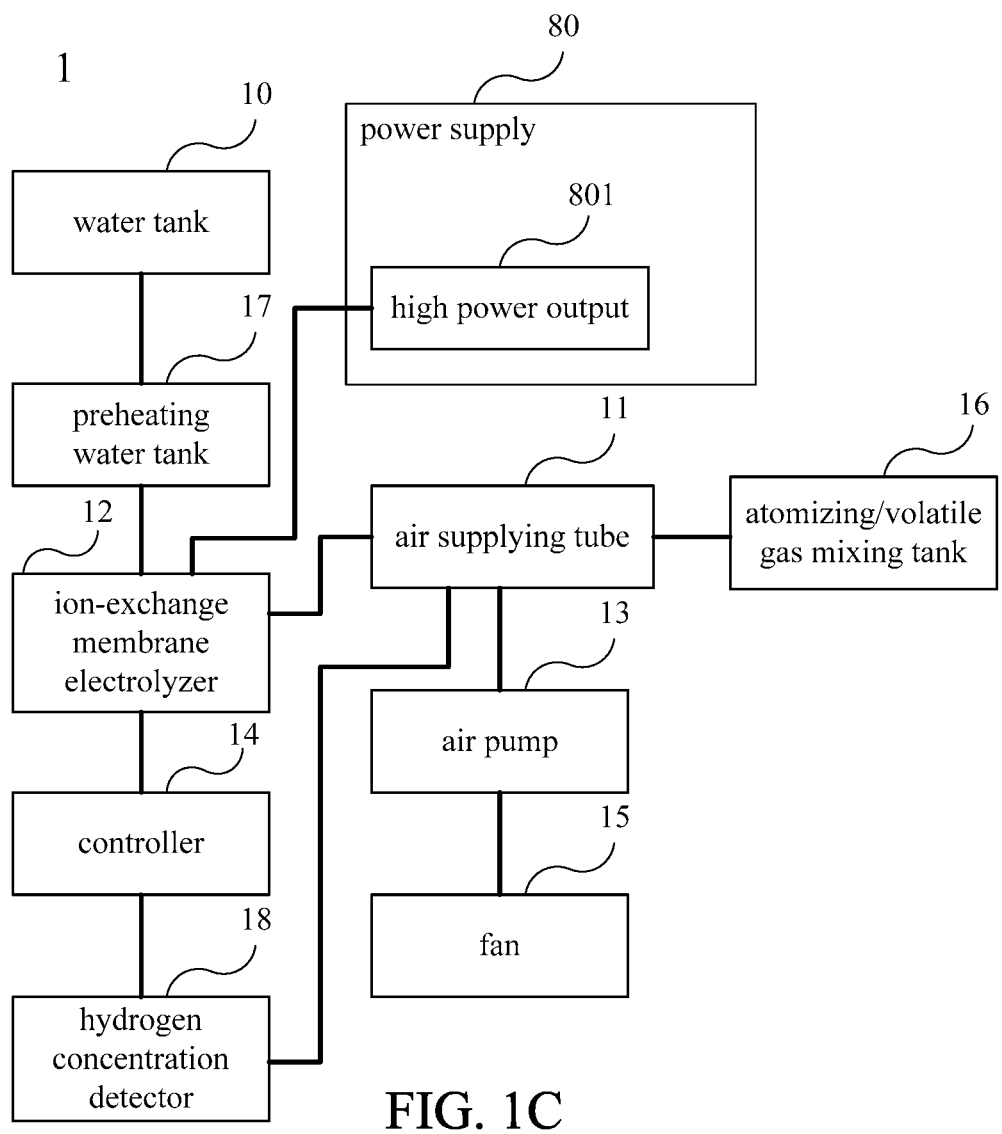
FIG. 1C is a functional block drawing illustrating the water electrolysis device according to an embodiment of the present invention.

Please refer to FIG. 1A to FIG. 1C. FIG. 1A is an appearance drawing illustrating a water electrolysis device according to an embodiment of the present invention. FIG. 1B is an appearance drawing illustrating the water electrolysis device without the case according to an embodiment of the present invention. FIG. 1C is a functional block drawing illustrating the water electrolysis device according to an embodiment of the present invention. In an embodiment, the present invention provides a water electrolysis device 1 including a case 100 and an operation panel 102. The case 100 includes a side wall 110 and a base 112. The case 100 includes a water tank 10 and an ion-exchange membrane electrolyzer 12 therein. The water tank 10 is configured for providing the water for electrolyzing of the ion-exchange membrane electrolyzer 12, and is configured in one side of the case 100 opposite to the operation panel 102. The ion-exchange membrane electrolyzer 12 is configured between the operation panel 102 and the water tank 10, and in a non-central position of the case 100. The ion-exchange membrane electrolyzer 12 is configured for electrolyzing water to generate hydrogen gas. In an embodiment, the water can be, but not limited to, deionized water, so that high-purity hydrogen gas can be prepared. In practical applications, any kind of water available can be adopted. Moreover, the present invention is not limited to the ion-exchange membrane electrolyzer, and other types of electrolyzer also can be adopted in the present invention.

Figures 2A, 2B:
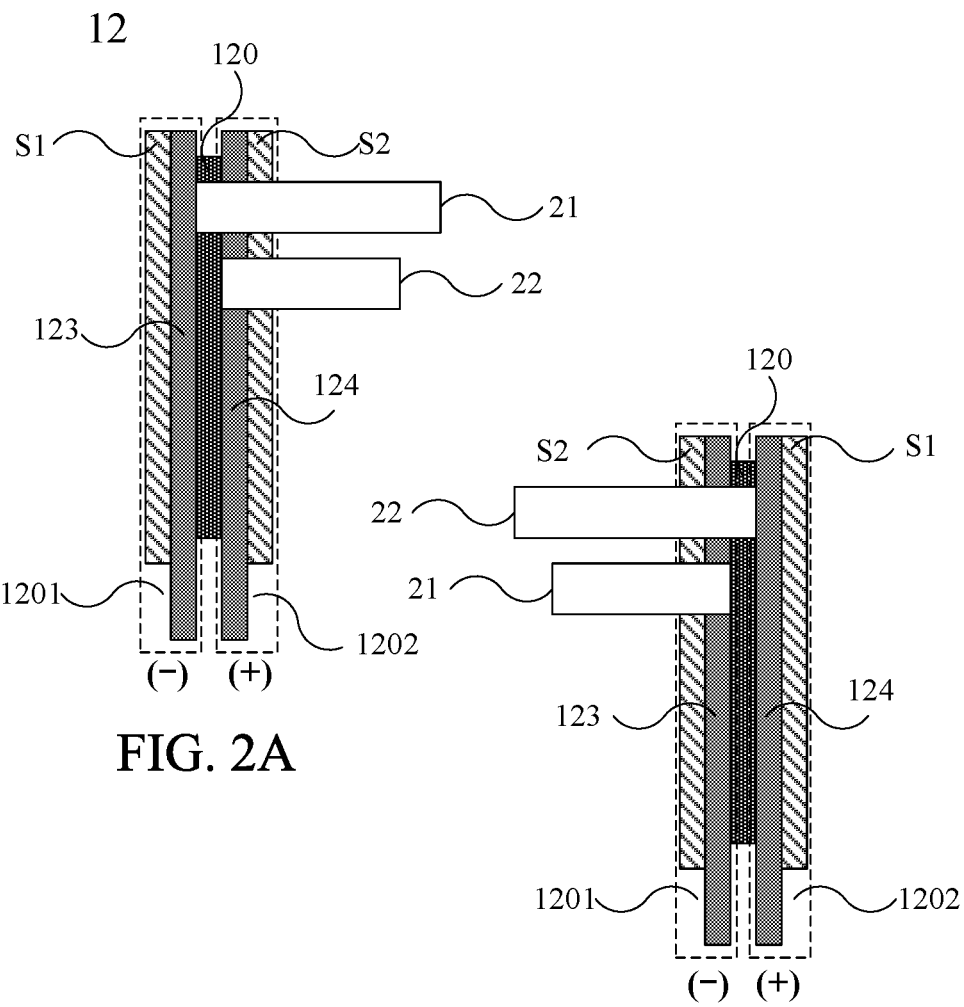
FIG. 2A is a simple sectional schematic drawing illustrating an ion-exchange membrane electrolyzer according to an embodiment of the present invention.
FIG. 2B is a simple sectional schematic drawing illustrating the ion-exchange membrane electrolyzer according to another embodiment of the present invention.

Please refer to FIG. 2A and FIG. 2B. FIG. 2A is a simple sectional schematic drawing illustrating the ion-exchange membrane electrolyzer according to an embodiment of the present invention. FIG. 2B is a simple sectional schematic drawing illustrating the ion-exchange membrane electrolyzer according to another embodiment of the present invention. This paragraph will cooperate with FIG. 2A and FIG. 2B to briefly explain the main feature of the present invention.

Please refer to FIG. 2A. The ion-exchange membrane electrolyzer 12 substantially includes an ion-exchange membrane 120, a cathode 123, an anode 124, a first side S1, a second side S2, a hydrogen output tube 21 and an oxygen output tube 22. The ion-exchange membrane 120 is configured between the first side S1 and the second side S2. The cathode 123 is configured between the ion-exchange membrane 120 and the first side S1, and the anode 124 is configured between the ion-exchange membrane 120 and the second side S2. The area where the first side S1 and the cathode 123 are located is referred as a cathode chamber 1201, and the area where the second side S2 and the anode 124 are located is referred as an anode chamber 1202. In order to express the corresponding positions of the cathode chamber 1201 and the anode chamber 1202 more clearly, the positions are indicated by broken lines in FIG. 2A. The hydrogen output tube 21 extends from the position between the ion-exchange membrane 120 and the first side S1 to the second side S2 and passes through the second side S2. The oxygen output tube 22 extends from the position between the ion-exchange membrane 120 and the second side S2 to the second side S2 and passes through the second side S2. While the ion-exchange membrane electrolyzer 12 electrolyzes water, the cathode 123 generates hydrogen gas, and the anode 124 generates oxygen gas. The main feature of the present invention is that the hydrogen gas and oxygen gas generated by electrolyzing water are outputted together from the second side S2 of the ion-exchange membrane electrolyzer 12 respectively via the hydrogen output tube 21 and the oxygen output tube 22. In this embodiment, the hydrogen output tube 21 and the oxygen output tube 22 are outputted together from one side of the anode chamber 1202 of the ion-exchange membrane electrolyzer 12.

However, the positions of the hydrogen output tube 21 and the oxygen output tube 22 of the present invention are not limited to the foregoing embodiments. Please refer to FIG. 2B. The ion-exchange membrane electrolyzer 12 shown in FIG. 2B has the components same with those shown in FIG. 2A. The difference is that the configured positions of the first side S1 and the second side S2 in FIG. 2B are opposite to those in FIG. 2A. It brings about the result that in FIG. 2B, the anode 124 is configured between the ion-exchange membrane 120 and the first side S1, and the cathode 123 is configured between the ion-exchange membrane 120 and the second side S2. The cathode chamber 1201 includes the second side S2 and cathode 123, and the anode chamber 1202 includes the first side S1 and the anode 124. The hydrogen output tube 21 extends from the position between the ion-exchange membrane 120 and the second side S2 to the second side S2 and passes through the second side S2. The oxygen output tube 22 extends from the position between the ion-exchange membrane 120 and the first side S1 to the second side S2 and passes through the second side S2. While the ion-exchange membrane electrolyzer 12 electrolyzes water, the cathode 123 generates hydrogen gas, and the anode 124 generates oxygen gas. The main feature of the present invention is that the hydrogen gas and oxygen gas generated by electrolyzing water are outputted together from the second side S2 of the ion-exchange membrane electrolyzer 12 respectively via the hydrogen output tube 21 and the oxygen output tube 22. In this embodiment, the hydrogen output tube 21 and the oxygen output tube 22 are outputted together from one side of the cathode chamber 1201 of the ion-exchange membrane electrolyzer 12.

That is to say, the hydrogen output tube 21 and the oxygen output tube 22 can be configured on any side of the ion-exchange membrane electrolyzer 12 in the present invention according to the practical requirement of the user.

Figure 2C:
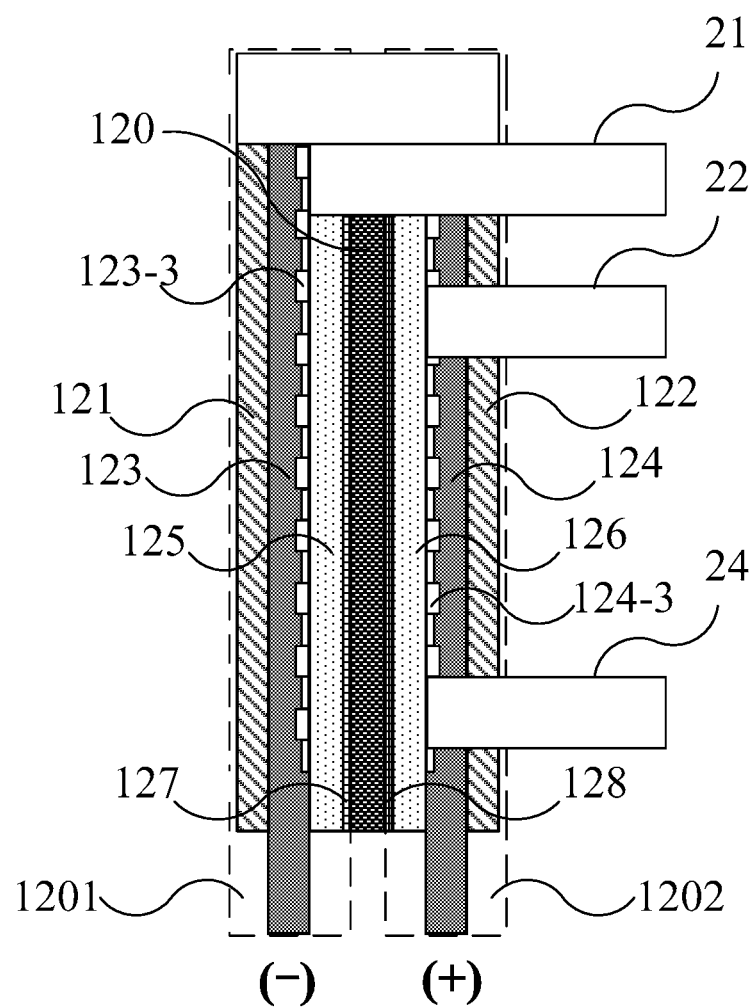
FIG. 2C is a sectional schematic drawing illustrating the ion-exchange membrane electrolyzer according to the embodiment of FIG. 2A.

Please refer to FIG. 2C. FIG. 2C is a sectional schematic drawing illustrating the ion-exchange membrane electrolyzer according to the embodiment of FIG. 2A. As shown in FIG. 2C, the ion-exchange membrane electrolyzer 12 includes an ion-exchange membrane 120, a cathode chamber 1201 and an anode chamber 1202. The cathode chamber 1201 includes a cathode 123, and the anode chamber 1202 includes an anode 124. The ion-exchange membrane 120 is configured between the anode chamber 1202 and the cathode chamber 1201. While the ion-exchange membrane electrolyzer 12 electrolyzes water, the cathode 123 generates hydrogen gas, and the anode 124 generates oxygen gas. In an embodiment, the anode chamber 1202 contains water, and the water in the anode chamber 1202 can further penetrate through the ion-exchange membrane to the cathode chamber 1201. In addition, FIG. 2A to FIG. 2C are only the sectional schematic drawings for explaining the internal structure of the ion-exchange membrane electrolyzer, but not the actual internal structure of the ion-exchange membrane electrolyzer. The blank block on the upper portion of FIG. 2C indicates the external case of the ion-exchange membrane electrolyzer 12.

As shown in FIG. 2C, the ion-exchange membrane 120 includes an ion-exchange membrane body 1203, a cathode catalytic layer 127 and an anode catalytic layer 128. The ion-exchange membrane body 1203 can be a proton exchange membrane, and preferably a Nafion membrane. The material of the cathode catalytic layer 127 can be selected from one or a combination from a group consisting of Pt, Ir, Pd and Pt alloy powders. The material of the anode catalytic layer 128 can be selected from one or a combination from a group consisting of Pt, Ir, Pd, Pt alloy powders and Carbon. In an embodiment, the materials of the cathode catalytic layer 127 or the anode catalytic layer 128 can be respectively configured as slurry coatings on both sides of the ion-exchange membrane to form the cathode catalytic layer 127 and the anode catalytic layer 128. In practical applications, the hydrogen gas can be generated on the catalytic layer, but not limited thereto. The hydrogen gas also can be generated on the electrode plate, or even between the ion-exchange membrane and the electrode plate. Therefore, comparing with the conventional alkali-type electrolyzer, the ion-exchange membrane electrolyzer 12 used in the present invention can avoid the problems of corrosion of the tank body, environmental pollution, incomplete filtration that causes the inhalation of the electrolyte-containing gas.

Please refer to FIG. 2A to FIG. 2C. The cathode chamber 1201 includes a cathode external plate 121, a cathode 123, a cathode sealing plate 125 and a cathode catalytic layer 127. The anode chamber 1202 includes an anode external plate 122, an anode 124, an anode sealing plate 126 and an anode catalytic layer 128. As shown in FIG. 2A, the first side S1 and the second side S2 respectively corresponds to the cathode external plate 121 and the anode external plate 122 in FIG. 2C. On the other hand, as shown in FIG. 2B, the first side S1 and the second side S2 in FIG. 2B respectively corresponds to the anode external plate 122 and the cathode external plate 121 in FIG. 2C. The ion-exchange membrane electrolyzer 12 includes a hydrogen output tube 21, an oxygen output tube 22 and a water supplying pipe 24. The oxygen output tube 22 is configured for outputting the oxygen gas, and the cathode output tube 21 is configured for outputting the hydrogen gas generated from the cathode chamber 1201. As shown in FIG. 2C, the hydrogen output tube 21 passes through the cathode sealing plate 125, the anode sealing plate 126, the anode 124 and the anode external plate 122 (the second side S2 in FIG. 2A), so as to connect the cathode chamber 1201 to the external environment outside the ion-exchange membrane electrolyzer 12 and output hydrogen gas. The oxygen output tube 22 is configured for outputting oxygen gas generated from the anode chamber 1202. The oxygen output tube 22 passes through the anode 124 and the anode external plate 122, so that the anode chamber 1202 can be connected to the external environment outside the ion-exchange membrane electrolyzer 12 and output oxygen gas. The water supplying pipe 24 passes through the anode 124 and the anode external plate 122, and is connected to the water tank 10 for guiding the water from the water tank 10 into the anode chamber 1202 to replenish the water for electrolyzing of the ion-exchange membrane electrolyzer 12. Both of the oxygen output tube 21 and the hydrogen output tube 22 are configured on the same side of the ion-exchange membrane electrolyzer 12. In this embodiment, all of the oxygen output tube 21, the hydrogen output tube 22 and the water supplying pipe 24 pass through and are configured on the anode external plate 122. However, the present invention is not limited to the aforementioned feature. For example, the oxygen output tube 21, the hydrogen output tube 22 and the water supplying pipe 24 also can pass through and be configured on the cathode external plate 121 in the similar structure, as shown on the second side S2 in FIG. 2B.

Figure 3:
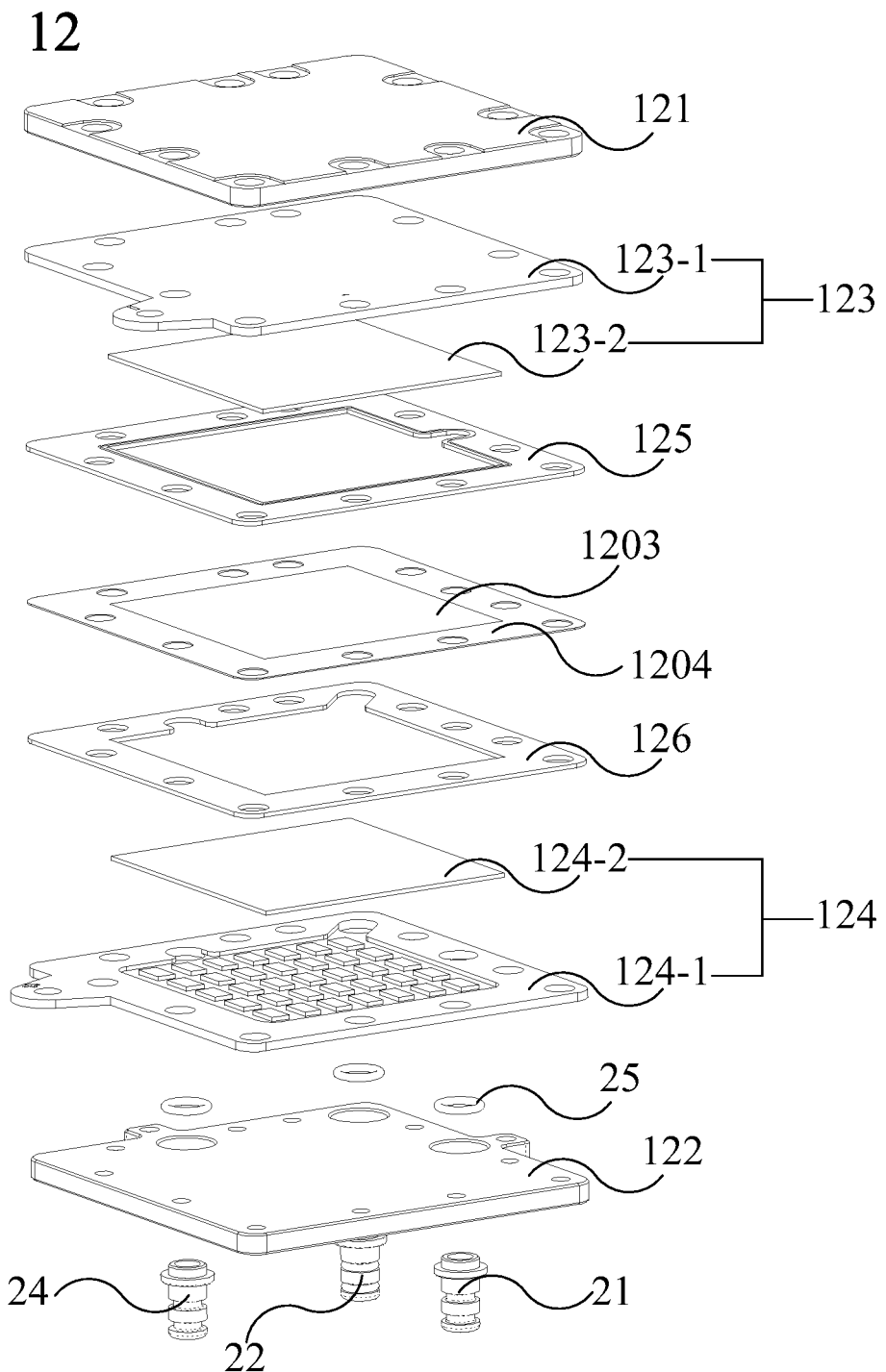
FIG. 3 is an exploded drawing illustrating the ion-exchange membrane electrolyzer according to an embodiment of the present invention.
Figure 4:
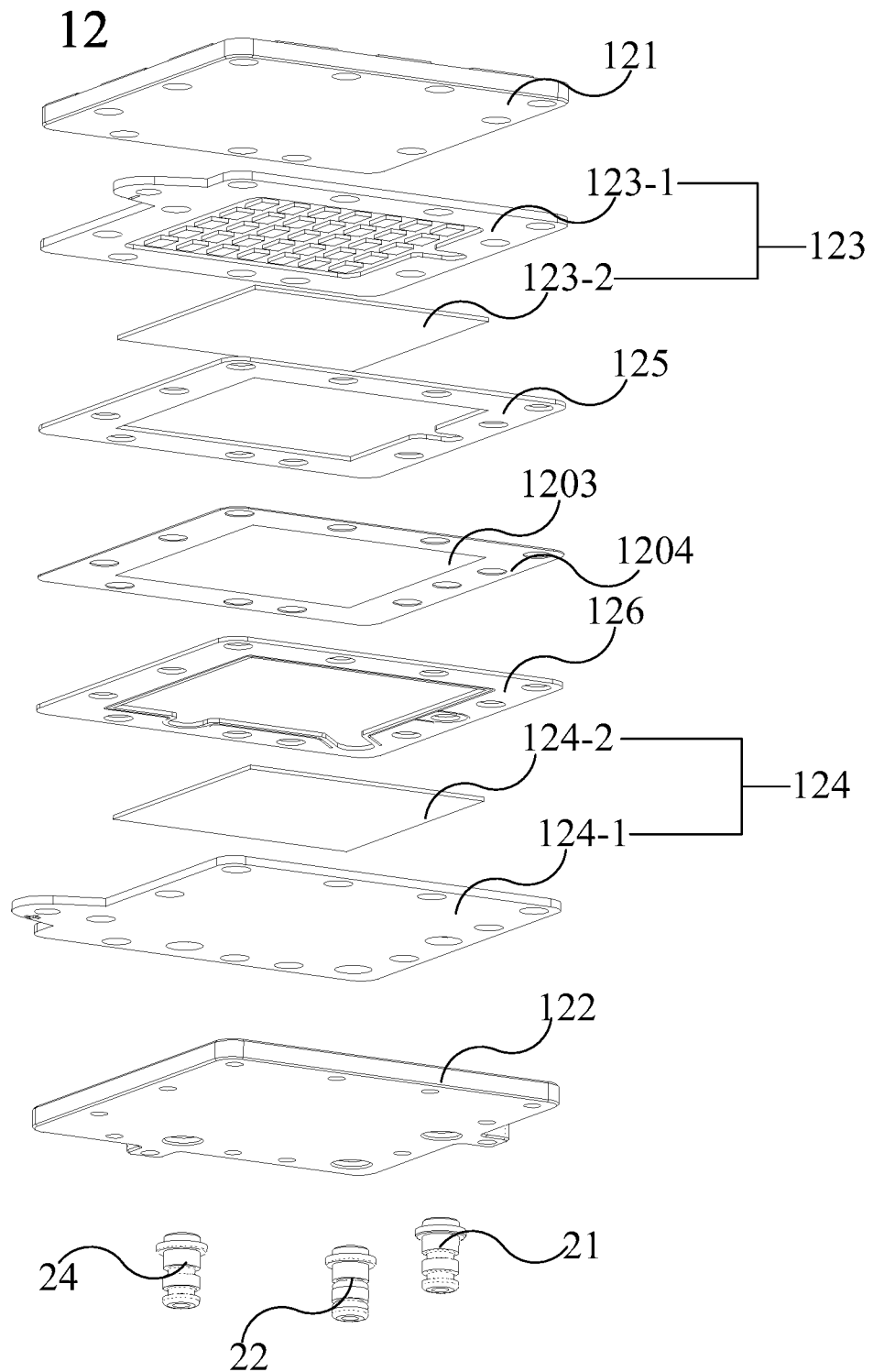
FIG. 4 is an exploded drawing illustrating the ion-exchange membrane electrolyzer in FIG. 3 from another perspective according to an embodiment of the present invention.

Please refer to FIG. 3 to FIG. 4. FIG. 3 is an exploded drawing illustrating the ion-exchange membrane electrolyzer according to an embodiment of the present invention. FIG. 4 is an exploded drawing illustrating the ion-exchange membrane electrolyzer in FIG. 3 from another perspective according to an embodiment of the present invention. The ion-exchange membrane 120 further includes an ion-exchange membrane external plate 1204 for fixing the relative positions of the ion-exchange membrane body 1203, the cathode catalytic layer 127 and the anode catalytic layer 128 in the ion-exchange membrane electrolyzer. FIG. 3 and FIG. 4 show the relationship of the positions of the components in the ion-exchange membrane electrolyzer 12 more clearly. The ion-exchange membrane electrolyzer 12 includes various components which can be assembled in the stacking sequence as shown in FIG. 3 and FIG. 4.

Please continue to refer to FIG. 3 to FIG. 4. In an embodiment, the ion-exchange membrane external plate 1204, the cathode sealing plate 125 and the anode sealing plate 126 can be arranged around the electrode plate to achieve insulation and airtightness, wherein the materials of the ion-exchange membrane external plate 1204, the cathode sealing plate 125 and the anode sealing plate 126 can be silicone. However, the configurations and materials of the cathode sealing plate 125 and the anode sealing plate 126 are not limited to the above embodiments. In practice, any configuration and material with insulation and airtightness effect can be adopted for the cathode sealing plate and the anode sealing plate.

As shown in FIG. 3 and FIG. 4, the hydrogen output tube 21 passes through the cathode sealing plate 125, the ion-exchange membrane external plate 1204, the anode sealing plate 126, the anode 124 and the anode external plate 122, so that the hydrogen gas generated in the cathode chamber 1201 can be outputted from the position where the anode external plate 122 is located via the hydrogen output tube 21. The oxygen output tube 22 passes through the anode 124 and the anode external plate 122, so that the oxygen gas generated in the anode chamber 1202 can be outputted from the position where the anode external plate 122 is located via the oxygen output tube 22 and the ion-exchange membrane external plate 1204. The water supplying pipe 24 passes through the anode 124 and the anode external plate 122, and is connected to the water tank 10 for guiding the water from the water tank 10 into the anode chamber 1202 to replenish the water of electrolyzing of the ion-exchange membrane electrolyzer 12. O-ring 25 are configured among the hydrogen output tube 21, the oxygen output tube 22 and the water supplying pipe 24 with the anode external plate 122 to seal the space among the hydrogen output tube 21, the oxygen output tube 22 and the water supplying pipe 24 with the anode external plate 122.

As shown in FIG. 3 and FIG. 4, the cathode 123 includes a cathode conductive plate 123-1 and a cathode electrode plate 123-2, and the anode 124 includes an anode conductive plate 124-1 and an anode electrode plate 124-2. In an embodiment, each electrode plate can be, but not limited to, a titanium powder die-casting sheet, and the material of each conductive plate can be, but not limited to, titanium. As shown in FIG. 3, in an embodiment, the cathode electrode plate 123-2 can be configured between the ion-exchange membrane 120 and the ion-exchange membrane body 1203 with the cathode conductive plate 123-1. The anode electrode plate 124-2 can be configured between the ion-exchange membrane 120 and the ion-exchange membrane body 1203 with the anode conductive plate 124-1. The ion-exchange membrane electrolyzer 12 can be connected to an outer power via the cathode conductive plate 123-1 and the anode conductive plate 124-1. In an embodiment, the anode conductive plate 124-1 (as shown in FIG. 3) and the cathode conductive plate 123-1 (as shown in FIG. 4) have flow channels respectively. When the cathode conductive plate 123-1 and the cathode electrode plate 123-2 are stacked on each other, a plurality of cathode chambers 123-3 can be formed in the cathode chamber 1201. When the anode conductive plate 124-1 and the anode electrode plate 124-2 are stacked on each other, a plurality of anode chambers 124-3 can be formed in the anode chamber 1202. The cathode chamber 123-3 and the anode chamber 124-3 can be configured for circulating gas and water therein, wherein the anode chamber 124-3 is connected to the oxygen output tube 22, and the cathode chamber 123-3 is connected to the hydrogen output tube 21.

Figure 5A:
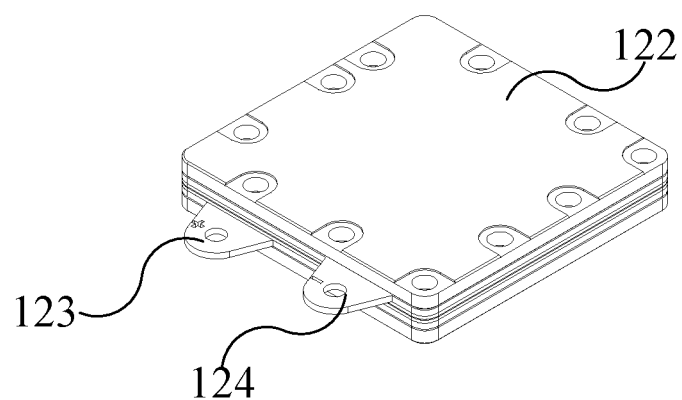
FIG. 5A and FIG. 5B are assembly drawings illustrating the ion-exchange membrane electrolyzer in FIG. 3 from different perspectives.
Figure 5B:
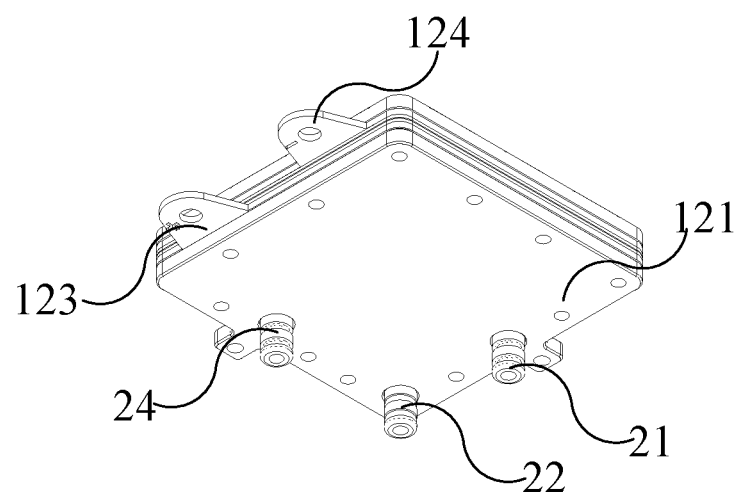
Figure 6:
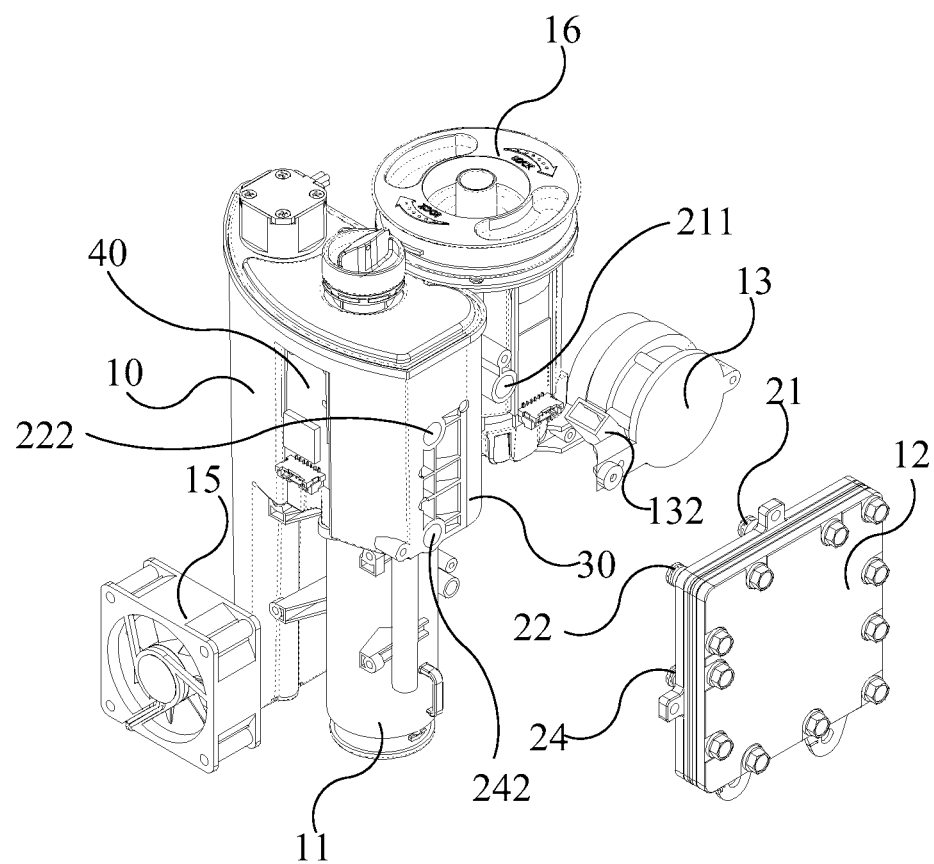
FIG. 6 is an exploded drawing illustrating the water electrolysis device according to an embodiment of the present invention.

Please refer to FIG. 5A and FIG. 5B. FIG. 5A and FIG. 5B are assembly drawings illustrating the ion-exchange membrane electrolyzer 12 in FIG. 3 from different perspectives. The cathode external plate 121 and the anode external plate 122 are configured respectively on two outer sides of the ion-exchange membrane electrolyzer 12 to fix and isolate the entire ion-exchange membrane electrolyzer 12, wherein the materials of the cathode external plate 121 and the anode external plate 122 can be stainless steel. In an embodiment, after the ion-exchange membrane electrolyzer 12 is assembled, it can be locked with a locking component (as shown in FIG. 6), but the number, type and locking way of the locking components are not limited to those shown in the figure (FIG. 6). As shown in the figure, the volume of the ion-exchange membrane electrolyzer 12 is relatively small. Therefore, the water electrolysis device is also compact in the present invention.

Figure 7A:
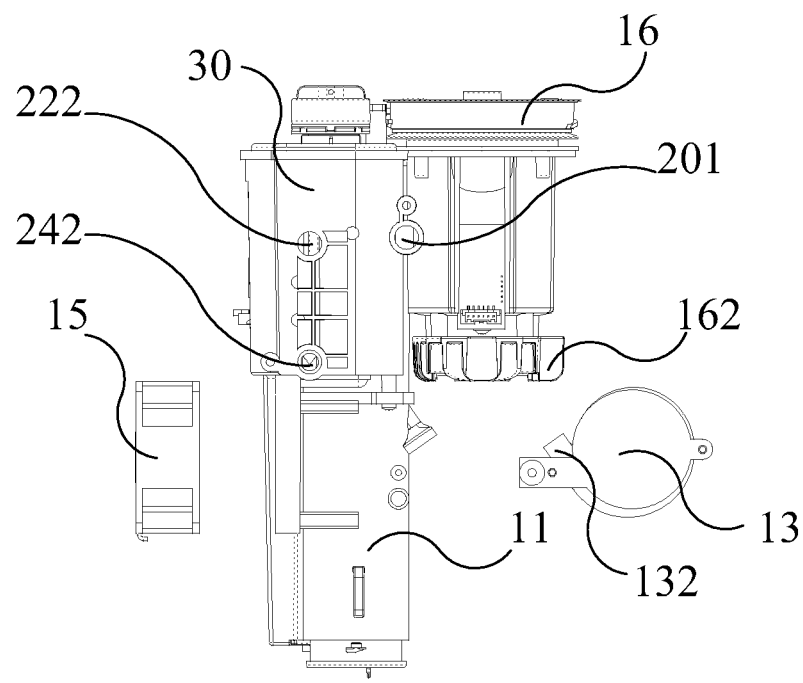
FIG. 7A and FIG. 7B are an exploded drawing and an assembly drawing respectively, illustrating the water electrolysis device in FIG. 6 from another perspective.
Figure 7B:
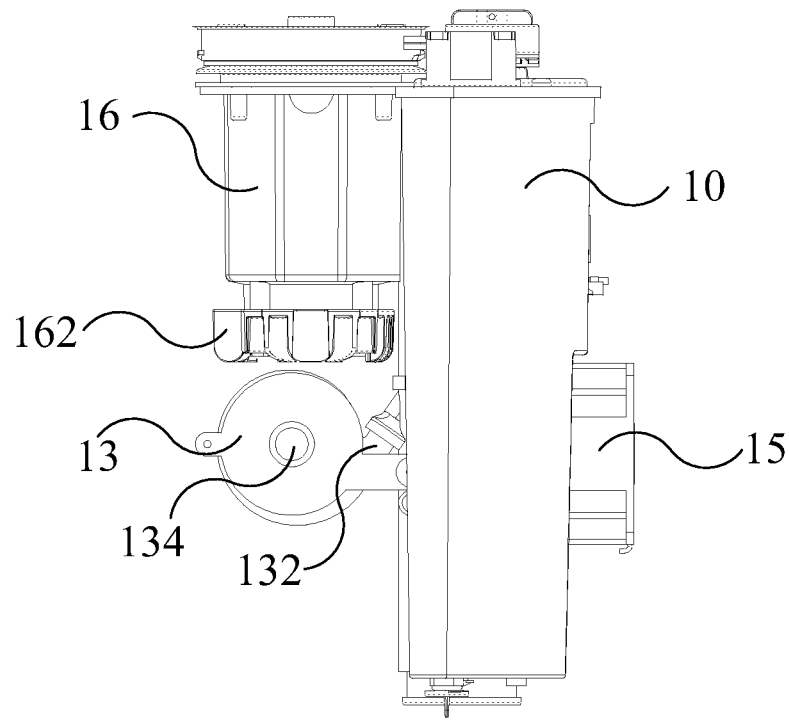

Please refer to FIG. 1C, FIG. 6, and FIG. 7A to FIG. 7B. FIG. 6 is an exploded drawing illustrating the water electrolysis device according to an embodiment of the present invention. FIG. 7A and FIG. 7B are the exploded drawings and the assembly drawings illustrating the water electrolysis device in FIG. 6 from another perspectives. For illustration, only necessary elements are shown in FIG. 6, FIG. 7A and FIG. 7B. The water electrolysis device 1 of the present invention also includes an air supplying tube 11, an air pump 13, a fan 15, an atomizing/volatile gas mixing tank 16, a hydrogen concentration detector 18, a controller 14, a gas-water separation tank 30 and a water level detecting device 40 in addition to the aforementioned water tank 10 and ion-exchange membrane electrolyzer 12. As shown in FIG. 6, the gas-water separation tank 30 is contained in the water tank 10, and its detailed structure will be described later. The water electrolysis device 1 of the present invention further includes a water level detecting device 40 which is configured for detecting the amount of water in the water tank 10. In one embodiment, the water level detecting device 40 is a capacitive water level detecting device and is configured on the outer surface of the water tank 10. The amount of water in the water tank 10 is measured by measuring the difference of capacitance between the water and the water-free area in the water tank 10.

Please refer to FIG. 6, FIG. 8A and FIG. 8B. FIG. 8A is a top view drawing illustrating the water electrolysis device according to an embodiment of the present invention. FIG. 8B is a sectional view drawing illustrating the water electrolysis device along the line D-D of FIG. 8A. The hydrogen output tube 21 of the ion-exchange membrane electrolyzer 12 is connected and communicated with the gas-water separation tank 30 via a hydrogen interface 211. The oxygen output tube 22 is connected and communicated with the water tank 10 via the oxygen interface 222. The water tank 10 includes a sterilizer 50. In this embodiment, the sterilizer 50 is a long-tube ultraviolet sterilizer configured in the water tank 10 away from the side where the gas-water separation tank 30 is located. The water supply pipe 24 directly communicates with the side near the sterilizer 50 of the water tank 10 via the water interface 242 to receive the sterilized water from the water tank 10 to replenish the water of electrolyzing of the ion-exchange membrane electrolyzer 12. In addition, as shown FIGS. 6, 7A, 7B, 8A, and 8B, the water electrolysis device 1 further comprises an integrated water tank module comprising a casing, the water tank 10 in the casing, the hydrogen interface 211 coupled to the casing, the oxygen interface 222 coupled to the casing, the water interface 242 coupled to the casing and the water tank 10, and the air supplying tube 11 coupled to the hydrogen interface 211.

The gas-water separation tank 30 includes a spring valve 32, a bobber 34 and a hydrogen discharge tube 36. The hydrogen gas generated by the ion-exchange membrane electrolyzer 12 is guided to the gas-water separation tank 30 via the hydrogen output tube 21 and the hydrogen interface 211. When the hydrogen gas in the gas-water separation tank 30 accumulates to a certain extent, the spring valve 32 will be opened due to the hydrogen gas pressure and allow the hydrogen gas to be discharged to the filter 60 via the hydrogen discharge tube 36 to filter impurities in the hydrogen gas. Furthermore, when the hydrogen gas is outputted from the ion-exchange membrane electrolyzer 12, a small amount of residual electrolyzed water may be contained in the hydrogen gas, and the residual electrolyzed water may accumulate in the gas-water separation tank 30 to form liquid water, so as to cause bobber 34 to float due to the accumulated liquid water. At this time, a drain port (not shown) covered by the bobber 34 will be opened, and the accumulated liquid water will be discharged into the water tank 10 through the drain port for recycling.

The oxygen gas generated by the electrolysis is directly discharged to the water tank 10 via the oxygen output tube 22 and the oxygen interface 222. The oxygen gas will be discharged to the atmospheric environment from the upper portion of the water tank 10. When the oxygen gas is outputted from the ion-exchange membrane electrolyzer 12, a small amount of residual electrolyzed water may be contained in the oxygen gas, and the residual electrolyzed water will be directly discharged into the water tank 10 for recycling.

Figure 9:
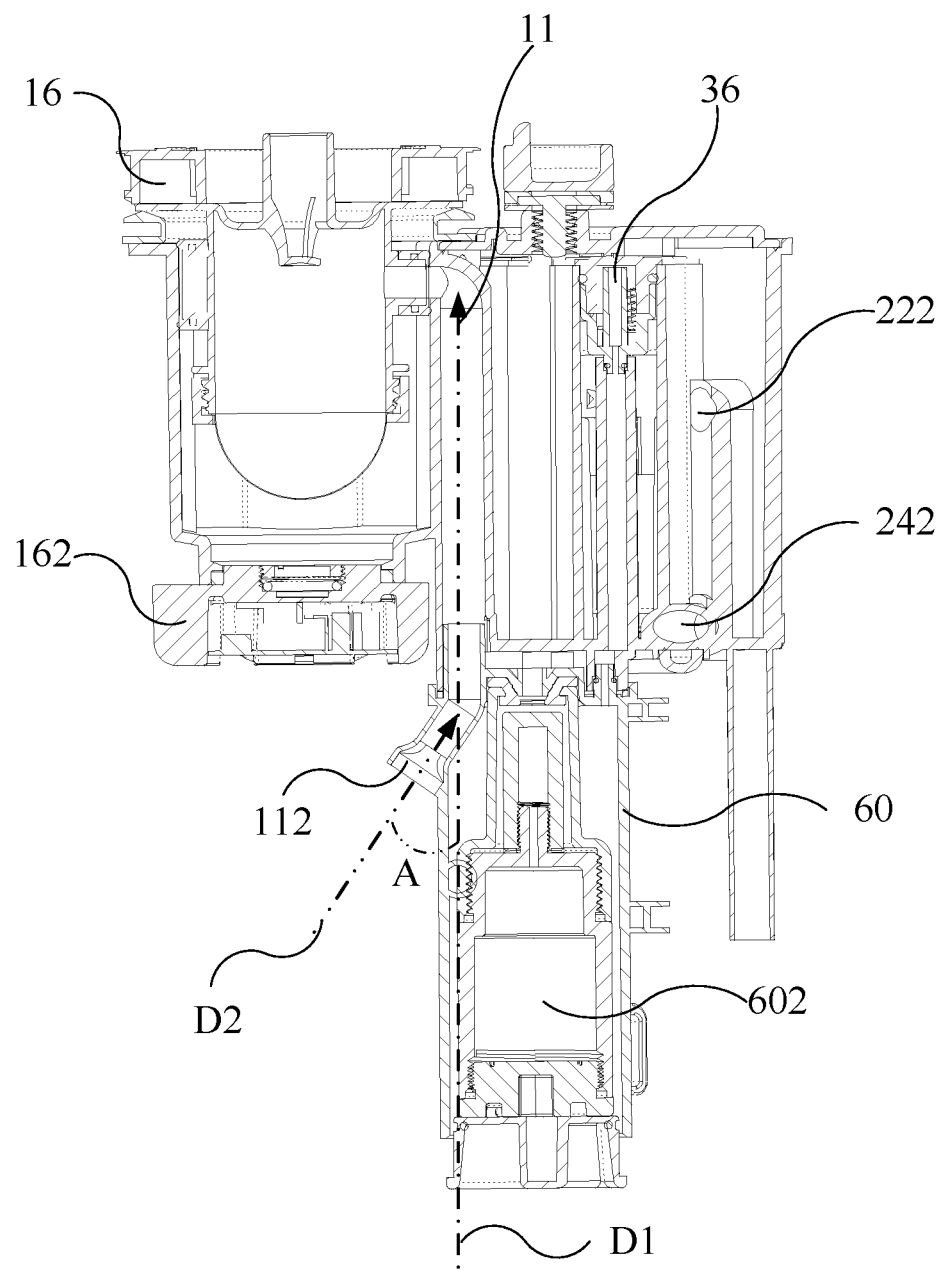
FIG. 9 is a sectional view drawing illustrating the water electrolysis device along the line Q-Q in FIG. 8A.

Please refer to FIG. 7A, FIG. 7B, FIG. 8A and FIG. 9 together. FIG. 9 is a sectional view diagram illustrating the water electrolysis device along the line Q-Q of FIG. 8A. As mentioned in the previous paragraph, the hydrogen gas is discharged to the filter 60 via the hydrogen discharge tube 36, and then a filter core 602 of the filter 60 filters the impurities in the hydrogen gas. The filtered hydrogen gas is further guided into the air supplying tube 11 for dilution and then guided into the atomizing/volatile gas mixing tank 16. The air supplying tube 11 is connected to the filter 60 to receive the filtered hydrogen gas, and the air supplying tube 11 is connected to the air pump 13. The fan 15 draws air from the external environment into the water electrolysis device 1 to dilute the hydrogen gas in the air supplying tube 11. All of the aforementioned components are covered by the case 100. The case 100 is set with a plurality of small holes. The fan 15 draws air from the external environment into the water electrolysis device 1 through the small holes on the case 100. The drawn air is guided into the air supplying tube 11 by the air pump 13. In this embodiment, the air pump 13 is a vortex fan, and the air drawn by the fan 15 is drawn into the air pump 13 through a drawing port 134 of the air pump 13, so as to guide air into the air supplying tube 11. As shown in FIG. 7B and FIG. 9, a duct 132 of the air pump 13 is connected with an air supplying interface 112 of the air supplying tube 11. The air supplying tube 11 has a first flow direction D1, and the air supplying interface 112 has a second flow direction D2. The first flow direction D1 points to the atomizing/volatile gas mixing tank 16, as indicated by the arrow on the indication line representing the first flow direction D1, and the arrow on the indication line also points to the position above the water electrolysis device. The second flow direction D2 points to the air supply tube 11, as indicated by an arrow on the indication line representing the second flow path direction D2, so that the air from the duct 132 through the air supplying interface 112 is guided into the air supplying tube 11. A lead angle A is formed between the first flow direction D1 and the second flow direction D2. The lead angle A is an acute angle less than 90 degrees, and preferably, between 25 to 45 degrees. At the connecting position of the air supplying tube 11 and the air supplying interface 112 where the lead angle A is located, the shape of the connecting position can be made as an arc lead angle. The air in the duct 132 and the air supplying interface 112 may be guided into the air supplying tube 11 by the design of the lead angle A to dilute the hydrogen gas in the air supplying tube 11.

Please continue to refer to FIG. 9. The atomizing/volatile gas mixing tank 16 is connected with the air supplying tube 11 to receive the filtered and diluted hydrogen gas, and generate an atomizing gas and mix it with the hydrogen gas to form a health gas, wherein the atomizing gas is selected from one or a combination from a group consisting of water vapor, atomizing potions and volatile essential oil. The atomizing/volatile gas mixing tank 16 includes an oscillator 162. The oscillator 162 atomizes water, atomizing potions or volatile essential oil in the atomizing/volatile gas mixing tank 16 by oscillation to generate the atomizing gas, and then the hydrogen gas is mixed with the atomizing gas to form a health gas. The atomizing/volatile gas mixing tank 16 can be selectively opened or closed according to users' requirements. That is to say, the atomizing/volatile gas mixing tank 16 can be activated by actuating the oscillator to provide the hydrogen gas mixing with the atomizing gas for the user, or can be closed by stopping the oscillator to provide the filtered and diluted hydrogen gas without mixing with the atomizing gas for the user. The means for user to inhale the filtered and diluted hydrogen or the health gas includes that the atomizing/volatile gas mixing tank 16 directly releases the hydrogen gas or health gas into the atmosphere, or provides for the user inhaling via a conduit and a mask.

The hydrogen concentration detector 18 is connected with the air supplying tube 11 to detect the hydrogen concentration in the air supplying tube 11. The controller 14 is connected to the hydrogen concentration detector 18, the air pump 13 and the ion-exchange membrane electrolyzer 12. In an embodiment, the hydrogen concentration detector 18 can be connected to the hydrogen output tube 21 or the hydrogen interface 211 to detect the volume concentration of the hydrogen gas outputted from the ion-exchange membrane electrolyzer 12 to the air supplying tube 11. The hydrogen concentration detector 18 detects whether the hydrogen volume concentration is within a range from a first predetermined value to a second predetermined value. For example, the first predetermined value is 4%, the second predetermined value is 6%, and the hydrogen concentration detected by the hydrogen concentration detector 18 ranges from 4% to 6%. The first predetermined value and the second predetermined value can be adjusted through the operation panel 102 according to the requirement of the user. In this embodiment, when the hydrogen concentration detector 18 detects that the volume of hydrogen gas in the hydrogen output tube 21 or the hydrogen interface 211 is higher than the first predetermined value by 4%, a first warning signal is generated to the controller 14. When the controller 14 receives the first warning signal, a start command is generated to the air pump 13 to start up the air pump 13 to draw air into the air supplying tube 11 to dilute the hydrogen gas in the air supplying tube 11. When the hydrogen concentration detector 18 detects that the volume of hydrogen gas in the hydrogen output tube 21 or the hydrogen interface 211 is higher than the second predetermined value by 6%, a second warning signal is generated to the controller 14. When the controller 14 receives the second warning signal, a stop command is generated to stop the ion-exchange membrane electrolyzer 12 by the means such as cutting off the power input to the ion-exchange membrane electrolyzer 12, and then the gas explosion due to the excessive hydrogen concentration can be avoided, thereby improving the overall safety.

Figure 10:
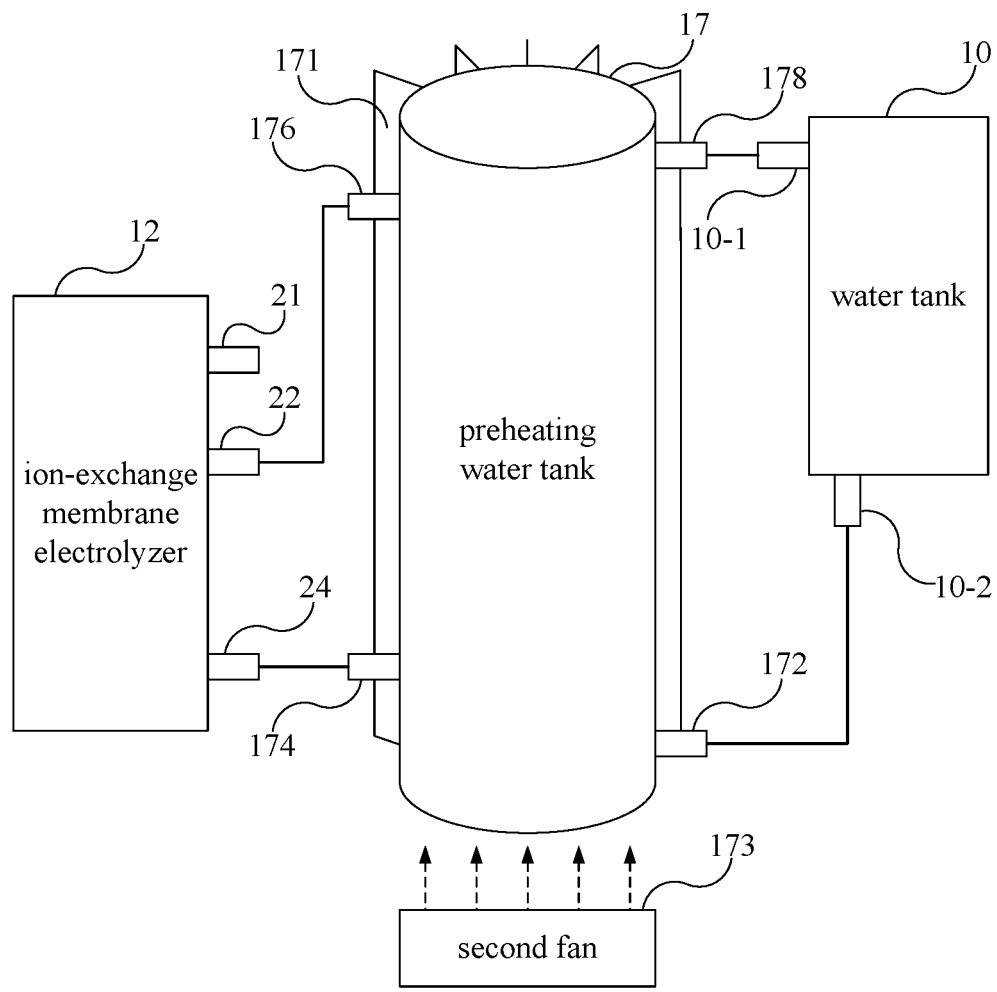
FIG. 10 is a sectional vie a schematic drawing illustrating the water electrolysis device according to another embodiment of the present invention.

Please refer to FIG. 10. FIG. 10 is a sectional view diagram illustrating the water electrolysis device according to another embodiment of the present invention. In another embodiment of the present invention, a preheating water tank 17 is further connected between the water tank 10 and the ion-exchange membrane electrolyzer 12. The preheating water tank 17 is substantially cylindrical or circular. Although the preheating water tank 17 is larger than the water tank 10 in FIG. 10, in other embodiments, the volume of the preheating water tank 17 can be smaller than that of the water tank 10. The preheating water tank 17 includes a preheating water tank water filling port 172 connected to the lower port 10-2 of the water tank 10, an electrolyzed water inlet 174 connected to the water supplying pipe 24 of the ion-exchange membrane electrolyzer 12, an oxygen receiving tube 176 connected to the oxygen output tube 22 and an oxygen discharge tube 178 connected to the upper port 10-1 of the water tank 10. The preheating water tank 17 is configured between the water tank 10 and the ion-exchange membrane electrolyzer 12. The electrolyzed water in the water tank 10 flows into the preheating water tank 17 first, and then flows into the ion-exchange membrane electrolyzer 12 through the electrolyzed water inlet 174 for electrolysis. The oxygen gas generated during the process of electrolyzing water and a portion of the residual electrolyzed water are discharged into the preheating water tank 17 via the oxygen receiving tube 176, wherein the portion of the residual electrolyzed water will remain in the preheating water tank 17. The oxygen gas generated by the electrolysis will be discharged to the water tank 10 via the oxygen discharge tube 178, and then discharged to the outside of the water electrolysis device.

Due to the process of electrolyzing water, the temperature of the ion-exchange membrane electrolyzer 12 will increase, and the temperature of the electrolyzed water is also related to the electrolysis efficiency. The temperature of electrolyzed water about 55 to 65° C. can improve the electrolysis efficiency. Thus, the preheating water tank 17 of the present invention recovers the higher temperature residual electrolyzed water discharged from the oxygen output tube 22 of the ion-exchange membrane electrolyzer 12 to preheat the electrolyzed water entering the ion-exchange membrane electrolyzer 12 in the preheating water tank 17 to an appropriate temperature, for example, between 55 and 65° C. In order to control the temperature of the electrolyzed water in the preheating water tank 17 to be maintained between 55 and 65° C., the preheating water tank 17 further includes a plurality of cooling fins 171 and a second fan 173. The plurality of cooling fins 171 are configured on the outer wall of the preheating water tank 17 in a radial pattern. The second fan 173 is configured at one end of the preheating water tank 17 and is matched with the plurality of cooling fins 171 to dissipate the preheating water tank 17 by forced convection. For the sake of simplicity, the cooling fins 171 are drawn only on a part of the outer wall of the preheating water tank 17. In other embodiments, the cooling fins 171 can be distributed all over the outer wall of the preheating water tank 17.

Figure 11:
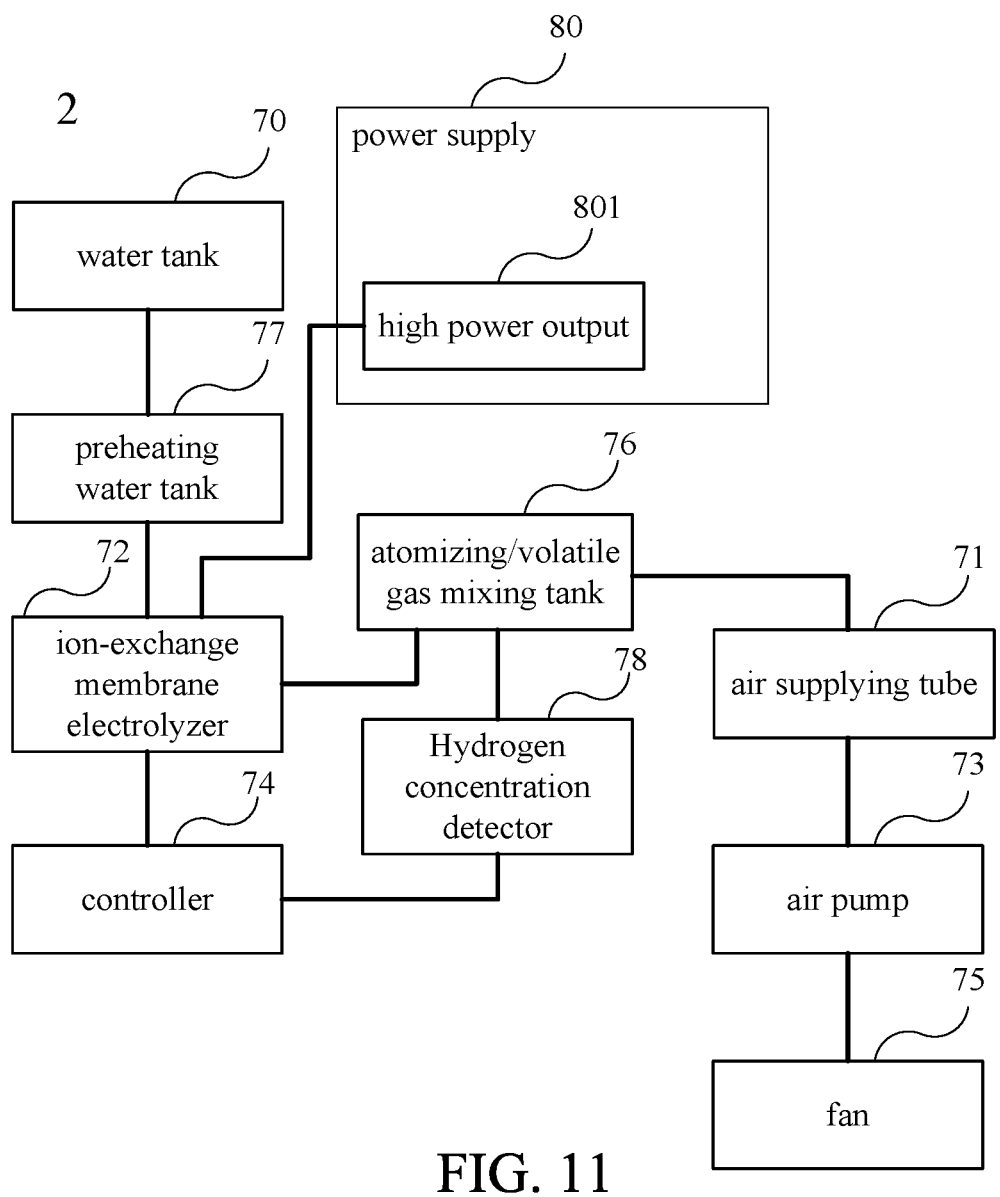
FIG. 11 is a functional block drawing illustrating the water electrolysis device according to another embodiment of the present invention.

Please refer to FIG. 11. FIG. 11 is a functional block drawing illustrating the water electrolysis device according to another embodiment of the present invention. The present invention provides another water electrolysis device 2 including a water tank 70, an ion-exchange membrane electrolyzer 72, an atomizing/volatile gas mixing tank 76, an air supplying tube 71, an air pump 73, a fan 75, a controller 74 and a preheating water tank 77. The difference between the water electrolysis device 2 and the water electrolysis device 1 is that the connecting relations among the ion-exchange membrane electrolyzer 72, the atomizing/volatile gas mixing tank 76, and the air supplying tube 71 of the water electrolysis device 2 are different from those of the ion-exchange membrane electrolyzer 12, the atomizing/volatile gas mixing tank 16, and the air supplying tube 11 of the water electrolysis device 1. The functions and connecting relations of the remaining components of the water electrolysis device 2 are the same as those of the water electrolysis device 1, and will not be described herein.

In the embodiment of the water electrolysis device 2, the ion-exchange membrane electrolyzer 72 is connected and communicated with the atomizing/volatile gas mixing tank 76 via the hydrogen output tube to receive the hydrogen gas generated by the ion-exchange membrane electrolyzer 72. The atomizing/volatile gas mixing tank 76 generates the atomizing gas and mixes it with the hydrogen gas to form a health gas, wherein the atomizing gas is selected from one or a combination from a group consisting of water vapor, atomizing potions and volatile essential oil. The atomizing/volatile gas mixing tank 76 includes an oscillator. The oscillator atomizes water, atomizing potions or volatile essential oil in the atomizing/volatile gas mixing tank 76 by oscillation to generate the atomizing gas, and then the hydrogen gas is mixed with the atomizing gas to form a health gas. The atomizing/volatile gas mixing tank 76 can be selectively opened or closed according to users' requirements. That is to say, the atomizing/volatile gas mixing tank 76 can be activated by actuating the oscillator to provide the hydrogen gas mixing with the atomizing gas for the user, or can be closed by stopping the oscillator to provide the filtered and diluted hydrogen gas without mixing with the atomizing gas for the user. The means for user to inhale the filtered and diluted hydrogen or the health gas includes that the atomizing/volatile gas mixing tank 76 directly releases the hydrogen gas or health gas into the atmosphere, or provides for the user inhaling via a conduit and a mask.

The hydrogen concentration detector 78 is connected with the atomizing/volatile gas mixing tank 76 to detect the hydrogen concentration in the atomizing/volatile gas mixing tank 76. The controller 74 is connected to the hydrogen concentration detector 78 and the ion-exchange membrane electrolyzer 72. In one embodiment, the hydrogen concentration detector 78 can be connected to the atomizing/volatile gas mixing tank 76 to detect the volume concentration of the hydrogen gas outputted from the ion-exchange membrane electrolyzer 72. The hydrogen concentration detector 78 detects whether the hydrogen volume concentration is within a range from a first predetermined value to a second predetermined value. For example, the first predetermined value is 4%, the second predetermined value is 6%, and the hydrogen concentration detected by the hydrogen concentration detector 78 ranges from 4% to 6%. The first predetermined value and the second predetermined value can be adjusted through the operation panel 102 according to the requirement of the user. In this embodiment, when the hydrogen concentration detector 78 detects that the volume of hydrogen gas in the atomizing/volatile gas mixing tank 76 is higher than the first predetermined value by 4%, a first warning signal is generated to the controller 74. When the controller 74 receives the first warning signal, a start command is generated to the air pump 13 to start up the air pump 13 to draw air into the air supplying tube 11 to dilute the hydrogen gas in the air supplying tube 11. When the hydrogen concentration detector 78 detects that the volume of hydrogen gas in the hydrogen output tube 21 or the hydrogen interface 211 is higher than the second predetermined value by 6%, a second warning signal is generated to the controller 74. When the controller 74 receives the second warning signal, a stop command is generated to stop the ion-exchange membrane electrolyzer 72 by the means such as cutting off the power input to the ion-exchange membrane electrolyzer 72, and then the gas explosion due to the excessive hydrogen concentration can be avoided, thereby improving the overall safety.

The air supplying tube 71 is connected to the atomizing/volatile gas mixing tank 76, and the air supplying tube 71 is further connected to the fan 75 and the air pump 73 for drawing the air from the external environment outside the water electrolysis device 2 to dilute the hydrogen gas in the atomizing/volatile gas mixing tank 76. The water electrolysis device 2 in the present invention includes a case which is configured for covering all of the aforementioned components. A plurality of small holes are configured on the case. The fan 75 draws the air from the external environment into the water electrolysis device 2 through the small holes on the case. The inhaled air is guided into the air supplying tube 71 by the air pump 73.

One of the purposes of the present invention is to reduce the volume of the water electrolysis device and the noise while maintaining sufficient hydrogen production, so that the user can use it during sleeping. Therefore, the applicant reduced the volume of the water electrolysis device as the main purpose first. For example, the water electrolysis device of the present case is roughly cylindrical. The longest section length at the bottom, that is, the diameter, is at least 200 mm, and the height of the device is up to 270 mm, so the volume is at most about 8,500 cubic centimeters, or 8.5 liters. However, the shape of the water electrolysis device of the present invention is not limited to the cylindrical type, and the shape of the water electrolysis device can be other shapes. For example, the water electrolysis device can be elliptical, square or polygonal, as long as the bottom or the longest sectional side of the base 112 is longer than the longest sectional side of the top to conform to the design of tapering from the bottom to the top. The effective use of the containing space defined by the case of the water electrolysis device is utilized as much as possible to maintain sufficient hydrogen production for the user. For example, the water electrolysis device has a total of six output settings for the hydrogen generating rates, including the hydrogen generating rate for the water electrolysis device outputting the health gas which mixes the air, the hydrogen gas and the atomizing gas: 120 ml/min, 240 ml/min, 360 ml/min, respectively, corresponding to three corresponding settings of the health gas outputting rate of the water electrolysis device: 2 L/min, 4 L/min and 6 L/min; and including the hydrogen generating rates for the water electrolysis device outputting the pure hydrogen gas: 400 ml/min, 500 ml/min, 600 ml/min. The user is allowed to adjust the hydrogen generation rate of the water electrolysis device 1 and the type of gas outputted through the operation panel. This device also reduces the noise, so that the user can place the present invention close to the user's head while sleeping.

Please refer to FIG. 1C and FIG. 11. In one embodiment, the present invention provides a water electrolysis device 1, 2 including a power supply 80 for converting supply mains to output 240 watts of direct current to supply power of the water electrolysis device 1, 2. The power supply 80 includes a high power output 801 and a low power output. The high power output 801 is connected to the ion-exchange membrane electrolyzer 12, 72 to supply the electric power required for the electrolysis reaction. The low power output is suitable for supplying electrical power to other non-electrolysis components in the water electrolysis device 1, 2, such as the air pump 13, the controller 14, the fan 15, and the hydrogen concentration detector 18. In order to simplify the content of the drawing, only the power supply 80 and the high power output 801 are illustrated in FIG. 1C and FIG. 11. One of ordinary skills in the art should be able to know the configuration of the low power output in the water electrolysis device to supply the power required for the operation of the water electrolysis device.

In the 240 watts of direct current supplied by the power supply 80, 172 watts are outputted from the high power output 801 to the ion-exchange membrane electrolyzer 12, 72. The high power output 801 outputs a first voltage and a first current, wherein the range of the first voltage is between 3 volts and 6.3 volts and the output of the first current is in a range from 10 amps to 27.3 amps. The low power output outputs 60 watts of direct current to supply the power required to operate the water electrolysis device. The low power output outputs a second voltage and a second current, wherein the second voltage is a DC voltage of 24 volts, and a second current is up to 2.5 amps. In another embodiment, the second voltage can also be reduced down from 24 volts to 5 volts and output a second current up to 0.5 amps. Comparing the power parameters outputted by the high power output with the low power output, the first voltage is lower than the second voltage, but the first current is higher than the second current. Therefore, the high power output outputs high-current low-voltage DC power, and the low power output outputs low-current high-voltage DC power.

With the examples and explanations mentioned above, the present invention provides a water electrolysis device including an ion-exchange membrane electrolyzer with the hydrogen gas and the oxygen gas outputted from the same side, an air supplying tube, an air pump, and an atomizing/volatile gas mixing tank. The ion-exchange membrane electrolyzer electrolyzes water to generate hydrogen gas. After inputting the hydrogen, the air pump draws air and inputs the air unidirectionally into the air supplying tube through a air supplying interface having a lead angle with the air supplying tube to dilute the hydrogen gas in the air supplying tube, and then the air supplying tube introduces the diluted hydrogen into the atomizing/volatile gas mixing tank and mixes with an atomizing gas for the user.

Through the ion-exchange membrane electrolyzer with the hydrogen gas and the oxygen gas outputted from the same side, the water tank, the gas-water separation tank, and the air supplying tube configured in a case within a defined volume, the water electrolysis device of the present invention employs the containing space in the case as much as possible while maintaining sufficient hydrogen production, and the fan and the air pump of water electrolysis device are also based on low noise. Therefore, this present invention actually provides a water electrolysis device with effective space arrangement, small volume and low noise, and the suitableness for placing beside the user.

The features and spirits of the present invention are hopefully described more clearly by the above detailed description of the preferred embodiments, and the scope of the present invention is not limited by the preferred embodiments disclosed above. On the contrary, the purpose is to cover a variety of changes and equivalence arrangements within the scope of the patent application to be applied for by the creative institute. Although the present invention has been disclosed in the above embodiments, it is not intended to limit the present invention, and anyone skilled in the art can make various changes and refinements without departing from the spirit and scope of the present invention. Therefore, the scope of protection of this present invention is subject to the definition of the scope of the patent application attached.

What is claimed is:

1. A water electrolysis device, comprising:
an integrated water tank module comprising a casing, a water tank in the casing, a hydrogen interface coupled to the casing, an oxygen interface coupled to the casing, a water interface coupled to the casing and the water tank, and a gas supplying tube coupled to the hydrogen interface, wherein the gas supplying tube comprises a gas supplying interface coupled to the casing;
an electrolyzer coupled to the integrated water tank module through the hydrogen interface, the oxygen interface and the water interface, wherein the electrolyzer outputs the hydrogen gas into the hydrogen interface and outputs the oxygen gas into the oxygen interface, and receives water from the water tank via the water interface to replenish the water in the electrolyzer during electrolyzing water; and
a pump coupled to the gas supplying interface to draw gas to the gas supplying interface to dilute the hydrogen gas in the gas supplying tube.

2. The water electrolysis device of claim 1, wherein the gas supplying tube has a first flow direction, the gas supplying interface has a second flow direction, the first flow direction points to the upper portion of the water electrolysis device, the second flow direction points to the gas supplying tube, a lead angle is formed between the first flow direction and the second flow direction.

3. The water electrolysis device of claim 2, wherein the lead angle formed between the first flow direction and the second flow direction is less than 90 degrees.

4. The water electrolysis device of claim 1, wherein the electrolyzer further comprises an anode chamber and an oxygen output tube, and the anode chamber comprises an anode including an anode conductive plate, an anode sealing plate, and an anode external plate; when the electrolyzer electrolyzes the water, the anode chamber generates oxygen gas; the oxygen output tube is configured for outputting the oxygen gas; and the oxygen output tube passes through the anode external plate, the anode conductive plate and the anode sealing plate.

5. The water electrolysis device of claim 4, wherein the electrolyzer further comprises a cathode chamber and a hydrogen output tube; the hydrogen output tube is configured for outputting the hydrogen gas; the cathode chamber comprises a cathode including a cathode conductive plate and a cathode sealing plate; the hydrogen output tube passes through the anode external plate, the anode conductive plate, the anode sealing plate and the cathode sealing plate, wherein the oxygen gas and the hydrogen gas are outputted on the same side of the electrolyzer.

6. The water electrolysis device of claim 4, wherein the electrolyzer further comprises a water supplying pipe; the water supplying pipe is configured on and passes through the anode external plate, the anode conductive plate and the anode sealing plate to connect the anode chamber and the water tank; and water from the water tank flows into the anode chamber through the water supplying pipe to replenish water in the anode chamber.

7. The water electrolysis device of claim 6, further comprising a water level detecting device; the water level detecting device being configured on the outer side of the water tank for detecting the amount of water in the water tank.

8. The water electrolysis device of claim 1, further comprising a fan drawing the gas from the environment outside the water electrolysis device such that the pump guiding the gas into the gas supplying tube.

9. The water electrolysis device of claim 1, further comprising:
a hydrogen concentration detector configured for detecting a volume concentration of the hydrogen gas and generating a first warning signal when the detected volume concentration of the hydrogen gas is higher than a first predetermined value; and
a controller coupled to the hydrogen concentration detector and configured for generating a start command to start up the pump when receiving the first warning signal.

10. The water electrolysis device of claim 1, further comprising:
a hydrogen concentration detector configured for detecting a volume concentration of the hydrogen gas and generating a second warning signal when the detected volume concentration of the hydrogen is higher than a second predetermined value; and
a controller coupled to the hydrogen concentration detector and configured for generating a stop command to stop the electrolyzer when receiving the second warning signal.

11. The water electrolysis device of claim 9, wherein the first predetermined value is 4%.

12. The water electrolysis device of claim 1, further comprising a power supply; the power supply comprising a high power output and a low power output, wherein the electric power outputted by the low power output is equal to or less than half of that outputted by the high power output; the high power output outputs a first voltage and a first current, the low power output outputs a second voltage and a second current, the first voltage is less than the second voltage, and the first current is greater than the second current.

13. The water electrolysis device of claim 1, further comprising an atomizing/volatile gas mixing tank coupled to the gas supplying tube and configured for receiving the diluted hydrogen gas, the atomizing/volatile gas mixing tank selectively generating an atomizing gas and mixing it with the diluted hydrogen gas to form a health gas, wherein the atomizing gas is water vapor, atomizing potions or volatile essential oil.

14. A water electrolysis device, comprising:
an integrated water tank module comprising a casing, a water tank in the casing, a hydrogen interface coupled to the casing, an oxygen interface coupled to the casing, a water interface coupled to the casing and the water tank, and an gas supplying tube coupled to the hydrogen interface;
an electrolyzer comprising a cathode, an anode, a hydrogen output tube, an oxygen output tube, and a water supplying pipe, the cathode generating hydrogen gas and the anode generating oxygen gas during electrolyzing water, wherein the hydrogen output tube outputs the hydrogen gas to the hydrogen interface, the oxygen output tube outputs the oxygen gas to the oxygen interface, and the water supplying pipe receives water from the water tank via the water interface to replenish the water in the electrolyzer; and a pump, the pump coupled to the gas supplying interface to draw gas to dilute the hydrogen gas received by the gas supplying tube from the hydrogen interface.

15. The water electrolysis device of claim 14, further comprising a case, the case comprising a base and a side wall, the electrolyzer being configured in a non-central position of the case, and a hydrogen generating rate of the water electrolysis device is between 120 ml/min and 600 ml/min.

16. The water electrolysis device of claim 15, wherein the electrolyzer further comprises a first side, a second side, and an ion-exchange membrane, the ion-exchange membrane is configured between the anode and the cathode, wherein the first side is close to the side wall, the oxygen gas and the hydrogen gas are outputted from the second side of the electrolyzer.

17. The water electrolysis device of claim 16, wherein the anode is configured between the ion-exchange membrane and the second side, the cathode is configured between the ion-exchange membrane and the first side, the oxygen output tube extends from the position between the ion-exchange membrane and the second side to the second side and passes through the second side, the hydrogen output tube extends from the position between the ion-exchange membrane and the first side to the second side and passes through the second side.

18. The water electrolysis device of claim 16, wherein the anode is configured between the ion-exchange membrane and the first side, the cathode is configured between the ion-exchange membrane and the second side, the hydrogen output tube extends from the position between the ion-exchange membrane and the second side to the second side and passes through the second side, the oxygen output tube extends from the position between the ion-exchange membrane and the first side to the second side and passes through the second side.

* * * * *